US00PP16655P2

(12) United States Plant Patent
Perkins

(10) Patent No.: US PP16,655 P2
(45) Date of Patent: Jun. 13, 2006

(54) ***ANGELONIA* PLANT NAMED 'CARTBAS DEPINK'**

(50) Latin Name: *Angelonia angustifolia*
Varietal Denomination: Cartbas Depink

(75) Inventor: Ralph Tyler Perkins, Gilroy, CA (US)

(73) Assignee: Goldsmith Seeds, INC., Gilroy, CA (US)

( * ) Notice: Subject to any disclaimer, the term of this patent is extended or adjusted under 35 U.S.C. 154(b) by 76 days.

(21) Appl. No.: 11/059,707

(22) Filed: Feb. 17, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent L. Bell
(74) *Attorney, Agent, or Firm*—Jondle & Associates P.C.

(57) ABSTRACT

An *Angelonia* cultivar particularly distinguished by having a deep pink flower color and a spreading plant habit is disclosed.

1 Drawing Sheet

Figure 1:
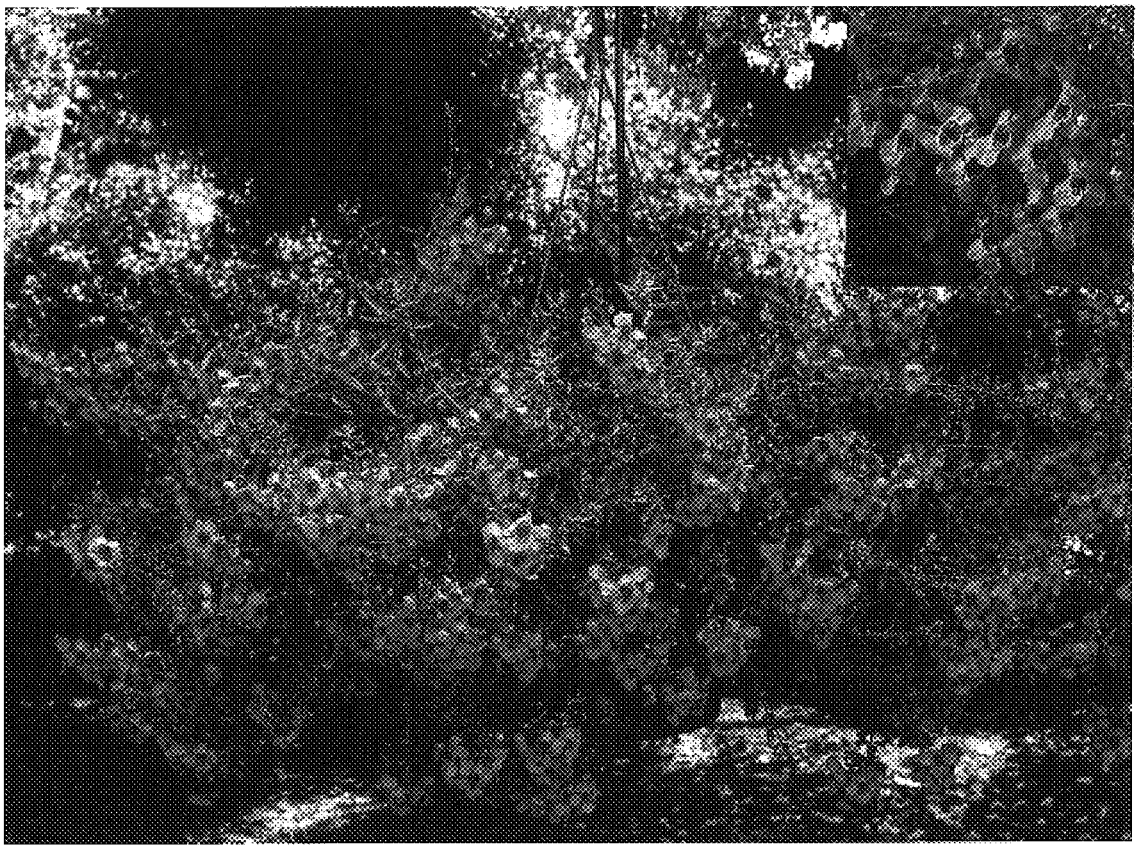

Genus and species: *Angelonia angustifolia.*
Variety denomination: 'Cartbas Depink'.

BACKGROUND OF THE NEW PLANT

The present invention comprises a new and distinct cultivar of *Angelonia,* botanically known as *Angelonia angustifolia,* and hereinafter referred to by the cultivar name 'Cartbas Depink'. The new cultivar originated from a cross between the unpatented proprietary *Angelonia* line 25-2 (female parent), which has rose-colored flowers, and the unpatented proprietary *Angelonia* line 60-1 (male parent), which has purple and white flowers.

The new cultivar was created and selected as a single plant within the progeny of the stated cross in 2001 in Gilroy, Calif. and has been asexually reproduced repeatedly in a controlled environment by vegetative cuttings and tissue culture in Gilroy, Calif. and Andijk, The Netherlands over a two-year period. The plant has also been trialed at Gilroy, Calif.; Litchfield, Mich. and Andijk, The Netherlands. 'Cartbas Depink' has been shown to reproduce true to type in successive generations of asexual propagation.

DESCRIPTION OF THE PHOTOGRAPH

This new *Angelonia* plant is illustrated by the accompanying photograph which shows the plant's form, foliage and flowers. The colors shown are as true as can be reasonably obtained by conventional photographic procedures.

FIG. 1 shows the mature plant's form, foliage and flowers. The inset is a closer view of the flowers.

DESCRIPTION OF THE NEW CULTIVAR

The following detailed description sets forth the distinctive characteristics of 'Cartbas Depink'. The data which define these characteristics were collected from asexual reproductions carried out in Gilroy, Calif. The detailed description was taken on 3–4 month old plants grown in one-gallon containers in a poly-covered greenhouse. Color readings were taken in natural light. Color references are primarily to The R.H.S. Colour Chart of The Royal Horticultural Society of London (R.H.S.), 2001 edition.

DETAILED BOTANICAL DESCRIPTION

Classification:
- *Family.*—Scrophulariaceae.
- *Botanical.*—*Angelonia angustifolia.*
- *Common.*—Angel flower.

Parentage:
- *Male parent.*—Proprietary line 60-1 (unpatented).
- *Female parent.*—Proprietary line 25-2 (unpatented).

Plant description:
- *Form.*—Prostrate and outwardly spreading.
- *Habit.*—Vigorous habit, well-branched; pinching 1–2 times after transplanting enhances branching.
- *Height.*—10–12 cm as measured from the base of the plant.
- *Width.*—50–55 cm as measured from the widest portion of the plant.

Propagation:
- *Time to initiate and develop roots.*—18–23 days.
- *Root description.*—Fibrous, free branching.
- *Time to produce a finished flowering plant.*—8–10 weeks for a 4–6 inch pot.
- *Outdoor plant performance.*—Does well in full sun; free-flowering through the summer; some heat tolerance. Use in mixed container plantings and hanging baskets.

Stems:
- *Length.*—30–35 cm as measured from the base of the plant.
- *Diameter.*—0.4 cm as measured at the midpoint of the stem.
- *Internode length.*—3.0–3.5 cm.
- *Color.*—RHS 144B.
- *Texture.*—Many glandular hairs of various sizes.
- *Stem anthocyanin.*—Appears on new/young growth at the bud stage, light brown.

Leaves:
- *Arrangement.*—Opposite.
- *Mature leaves.*—Length, fully expanded: 8–9.5 cm. Width: 1.3–1.4 cm. Shape: Linear, slightly elliptic. Margin: Serrate. Apex: Acute. Base: Cuneate. Color: Upper surface: RHS 137A. Lower surface: RHS 137B. Texture: Many glandular hairs of various sizes. Venation: Pinnate. Venation color: RHS 137A in the leaf; (Lower surface) RHS 144B midvein (Entire lower surface and towards base on upper surface).

Flower bud:

*Shape.*—Orbicular.

*Diameter.*—0.5 cm.

*Length.*—0.6–0.7 cm.

*Color at tight bud.*—RHS 144C.

Inflorescence:

*Blooming habit.*—Continuous throughout the growing season; good floriferousness.

*Lastingness of individual blooms.*—6–9 days.

*Fragrance.*—None.

*Inflorescence type.*—Terminal raceme.

*Floret type.*—Single flowers; mostly two in a leaf axis; 5 petals fused at the base.

*Florets per raceme.*—46–50.

*Floret (limb) diameter.*—1.9–2.1 cm.

*Floret depth.*—0.8 cm.

Flower description:

*Flower color.*—Upper surface: Closest to RHS 68B with a spot of RHS 64B on the lower mid-petal lobe and a RHS 143B spot on the inside of this lobe. Lower surface: Closest to RHS 65A.

*Corolla color inside.*—RHS 155C but whiter, with RHS 65A spots.

*Petals.*—Size: Upper lip: Length: 0.7 cm from the corolla opening. Width: 1.0 cm. Lower lip, lateral petal: Length: 0.8 cm from the corolla opening. Width: 0.9 cm. Lower lip, mid-petal: Length: 1.0 cm from corolla opening. Width: 1.1 cm. Apex: Rounded. Base: Fused. Margin: Entire. Texture: Papillose with short glandular hairs.

*Sepals.*—Sepal number: 5, fused at base. Color (Upper surface): RHS 138A. Length: 0.4–0.5 cm. Width: 0.2 cm. Shape: Lanceolate. Apex: Acute. Margin: Entire. Anthocyanin: Deep purple brown, deepest at base fading to none at apex. Texture: Many short glandular hairs.

*Pedicels.*—Color: RHS 187C at the bud stage; fades to RHS 144A as it matures. Length: 1.5 cm. Diameter: 0.1 cm. Texture: Many gladular hairs of various sizes.

Reproductive organs:

*Stamens.*—4, in pairs.

*Filament color.*—RHS 155C but whiter.

*Filament length.*—0.35 cm.

*Anther color.*—RHS 164A.

*Pollen amount.*—Scarce.

*Pistil.*—One.

*Pistil length.*—0.30–0.35 cm.

*Stigma color.*—RHS 155C but whiter.

*Style color.*—RHS 155C but whiter.

Disease and insect resistance: Not observed.

COMPARISON WITH PARENTAL LINES AND KNOWN CULTIVARS

'Cartbas Depink' differs from the female parent, proprietary line 25-2 (unpatented), in that 'Cartbas Depink' has a spreading plant habit and a deep pink flower color while proprietary line 25-2 has a broad upright habit and a rose flower color. 'Cartbas Depink' differs from the male parent, proprietary line 60-1 (unpatented) in that 'Cartbas Depink' has a spreading plant habit and a deep pink flower color while proprietary line 60-1 has a more upright plant habit and a purple and white flower color.

'Cartbas Depink' is most similar to the commercial cultivar 'Balanglapi' (U.S. Plant Pat. No. 13,920); however, there are differences. 'Cartbas Depink' has a more prostrate habit, smaller foliage size, larger flower size and lighter pink flower color than 'Angelmist Lavender Pink'.

I claim:

1. A new and distinct *Angelonia* plant as shown and described herein.

* * * * *